United States Patent
Wolber et al.

(10) Patent No.: US 11,615,882 B2
(45) Date of Patent: Mar. 28, 2023

(54) APPARATUS, NON-TRANSITORY COMPUTER-READABLE STORAGE MEDIUM, AND COMPUTER-IMPLEMENTED METHOD FOR DISTRIBUTED LEDGER MANAGEMENT OF NUCLEAR MEDICINE PRODUCTS

(71) Applicant: GE Healthcare Limited, Buckinghamshire (GB)

(72) Inventors: Jan Wolber, Rickmansworth (GB); Scott Lagona, Brookfield, WI (US)

(73) Assignee: GE HEALTHCARE LIMITED, Buckinghamshire (GB)

( * ) Notice: Subject to any disclaimer, the term of this patent is extended or adjusted under 35 U.S.C. 154(b) by 619 days.

(21) Appl. No.: 16/183,188

(22) Filed: Nov. 7, 2018

(65) Prior Publication Data
US 2020/0143937 A1 May 7, 2020

(51) Int. Cl.
G16H 40/20 (2018.01)
G06Q 30/06 (2012.01)
(Continued)

(52) U.S. Cl.
CPC .............. *G16H 40/20* (2018.01); *A61K 9/51* (2013.01); *C40B 30/06* (2013.01); *G06Q 10/087* (2013.01); *G06Q 30/0607* (2013.01)

(58) Field of Classification Search
None
See application file for complete search history.

(56) References Cited

U.S. PATENT DOCUMENTS 9,667,427 B2  5/2017  Oberhauser et al.
9,703,986 B1  7/2017  Ashley et al.
(Continued)

FOREIGN PATENT DOCUMENTS

CN   106682530   5/2017
CN   107330701   11/2017
(Continued)

OTHER PUBLICATIONS

Haubner, Roland. "PET radiopharmaceuticals in radiation treatment planning—Synthesis and biological characteristics" (2010) Radiotherapy and Oncology 96, pp. 280-287. (Year: 2010).*
(Continued)

*Primary Examiner* — Allison G Wood
*Assistant Examiner* — Katherine A Barlow
(74) *Attorney, Agent, or Firm* — Hanley, Flight and Zimmerman, LLC

(57) ABSTRACT

Systems and methods for tracking and management of a distributed ledger including information for a batch of radiopharmaceutical material are disclosed. Certain examples provide a computer-implemented method of managing radiopharmaceutical material including tracking, using at least one processor, a status of a batch of radiopharmaceutical material, the status to include a type, a quantity, and a timestamp associated with the batch of radiopharmaceutical material; generating a record in a first copy of a distributed ledger using the type, quantity, and timestamp associated with the batch of radiopharmaceutical material; updating the record based on at least one of usage of the batch of radiopharmaceutical material, resale of at least a portion of the batch of radiopharmaceutical material, and decay of the batch of radiopharmaceutical material; and sharing the record with a second copy of the distributed ledger.

17 Claims, 11 Drawing Sheets

(51) Int. Cl.
  *A61K 9/51* (2006.01)
  *C40B 30/06* (2006.01)
  *G06Q 10/08* (2012.01)
  *G06Q 30/0601* (2023.01)
  *G06Q 10/087* (2023.01)

(56) References Cited

U.S. PATENT DOCUMENTS

| | | | |
|---|---|---|---|
| 9,749,140 B2 | 8/2017 | Oberhauser et al. | |
| 9,876,775 B2 | 1/2018 | Mossbarger | |
| 10,465,561 B2 | 11/2019 | Mervant et al. | |
| 2005/0096941 A1* | 5/2005 | Tong | G16H 70/40 705/2 |
| 2011/0029445 A1* | 2/2011 | Whittacre | G09B 7/00 705/317 |
| 2013/0102772 A1* | 4/2013 | Eshima | G21G 1/10 536/28.2 |
| 2013/0123719 A1* | 5/2013 | Mao | G16H 40/67 604/304 |
| 2014/0243500 A1 | 8/2014 | Engell et al. | |
| 2017/0005804 A1 | 1/2017 | Zinder | |
| 2017/0262862 A1 | 9/2017 | Aljawhari | |
| 2018/0060496 A1 | 3/2018 | Bulleit et al. | |
| 2018/0075028 A1 | 3/2018 | Ruschin et al. | |
| 2018/0082023 A1 | 3/2018 | Curbera et al. | |
| 2018/0082024 A1 | 3/2018 | Curbera et al. | |
| 2018/0082043 A1 | 3/2018 | Witchey et al. | |
| 2018/0082290 A1 | 3/2018 | Allen et al. | |
| 2018/0089374 A1 | 3/2018 | Gibson | |
| 2018/0096175 A1* | 4/2018 | Schmeling | G06Q 10/08 |
| 2018/0096347 A1* | 4/2018 | Goeringer | H04L 9/3247 |
| 2018/0264347 A1 | 9/2018 | Tran et al. | |
| 2018/0349845 A1* | 12/2018 | Klein | G08G 5/0069 |

FOREIGN PATENT DOCUMENTS

| | | |
|---|---|---|
| CN | 107368750 | 11/2017 |
| CN | 107391944 | 11/2017 |
| JP | 2018106642 A * | 7/2018 |
| WO | 2013048954 | 4/2013 |

OTHER PUBLICATIONS

Castillo, Michael. "Inside the Blockchain Factory: How IBM's Distributed Ledger Work Went Global" CoinDesk.com (Year: 2017).*
Nichol, Peter. "Teleradiology platforms: the business case for blockchain" CIO.com (Year: 2016).*
Al Ahmed, Ali, et al. "Improving efficiency management of radiopharmaceutical materials at a nuclear medicine department" BMJ Quality Improvement Reports, doi: 10.1136/bmjquality.u208970. w3709 (Year: 2015).*
Clark, Birgit et al., "Blockchain, IP and the pharma industry—how distributed ledger technologies can help secure the pharma supply chain" Journal of Intellectual Property Law & Practice, vol. 13, Issue 7, pp. 531-533, https://doi.org/10.1093/jiplp/jpy069 (Year: 2018).*
International Searching Authority, "International Search Report and Written Opinion," issued in connection with PCT patent application No. PCT/EP2019/058110, dated Nov. 18, 2019, 16 pages.
B. Amaraesekera et al., "High-Pressure, Compact, Modular Radiosynthesizer for production of positron emitting biomarkers," Applied Radiation and Isotopes, vol. 78, Apr. 25, 2013, 14 pages.
Claggett et al., "Simplified programming and control of automated radiosynthesizers through unit operations background," EJNMMI Research, vol. 3, Jul. 15, 2013, 14 pages.
Lazari et al., "Fully Automated Production of Diverse 18F-Labeled PET tracers on the ELIXYS Multireactor Radiosynthesizer Without Hardware Modification," Journal of Nuclear Medicine Technology, vol. 42, No. 3, Jul. 17, 2014, 10 pages.
Lindsey, "A retrospective on the automation of laboratory synthetic chemistry," Oct. 1, 1992, 32 pages.
Lazari M. S., "Thinking inside the "box": Development and implementation of a novel automated radiosynthesizer for 18F-labeled positron emission tomography tracers," Jan. 1, 2015, 238 pages.
International Searching Authority, "Search Report and Written Opinion," issued in connection with PCT patent application No. PCT/EP2019/080613, dated Jan. 17, 2020, 13 pages.

* cited by examiner

APPARATUS, NON-TRANSITORY COMPUTER-READABLE STORAGE MEDIUM, AND COMPUTER-IMPLEMENTED METHOD FOR DISTRIBUTED LEDGER MANAGEMENT OF NUCLEAR MEDICINE PRODUCTS

FIELD OF THE DISCLOSURE

This disclosure relates generally to improved nuclear medicine and, more particularly, to improved systems and methods for distributed ledger management of nuclear medicine products.

BACKGROUND

Nuclear medicine involves radioactive material to highlight aspects of a patient anatomy in a resulting image. Such radioactive material is expensive to produce, potentially hazardous, and rapidly decaying. As a result, radioactive material composition, production, storage, and usage are very tightly regulated and controlled, and its usable shelf-life is time-limited. Given the tight controls and rapid decay, material often goes unused due to delays in logistics and/or lack of communication. Furthermore, providers lose visibility into the state of the material, its use, etc., once the material is produced and distributed. This creates waste, uncertainty, and potential safety hazards, for example. Also, the value of any batch of a nuclear medicine tracer is directly related to its activity. Therefore it is desirable for producers and users to have timely information about activity in the process of ordering, distributing and using these materials.

BRIEF DESCRIPTION

Certain examples provide systems and methods for tracking and management of a distributed ledger including information for a batch of radiopharmaceutical material.

Certain examples provide a distribution monitoring processor apparatus including a data storage to store instructions for execution and a first copy of a distributed ledger; a data communication interface to receive and transmit data; a material status monitor to track a status of a batch of radiopharmaceutical material, the material status monitor to receive an indication of a type, a quantity, and a timestamp associated with the batch of radiopharmaceutical material via the data communication interface; and a ledger record processor to generate and update a record in the first copy of the distributed ledger using the indication of type, quantity, and timestamp associated with the batch of radiopharmaceutical material from the material status monitor, the ledger record processor to add a transaction to the record to track when and what quantity of the batch of radiopharmaceutical material is sold and resold.

Certain examples provide a computer-readable storage medium including instructions which, when executed, cause at least one processor to at least: track a status of a batch of radiopharmaceutical material, the status to include a type, a quantity, and a timestamp associated with the batch of radiopharmaceutical material; generate a record in a first copy of a distributed ledger using the type, quantity, and timestamp associated with the batch of radiopharmaceutical material; update the record based on at least one of usage of the batch of radiopharmaceutical material, resale of at least a portion of the batch of radiopharmaceutical material, and decay of the batch of radiopharmaceutical material; and share the record with a second copy of the distributed ledger.

Certain examples provide a computer-implemented method of managing radiopharmaceutical material. The example method includes tracking, using at least one processor, a status of a batch of radiopharmaceutical material, the status to include a type, a quantity, and a timestamp associated with the batch of radiopharmaceutical material. The example method includes generating, using the at least one processor, a record in a first copy of a distributed ledger using the type, quantity, and timestamp associated with the batch of radiopharmaceutical material. The example method includes updating, using the at least one processor, the record based on at least one of usage of the batch of radiopharmaceutical material, resale of at least a portion of the batch of radiopharmaceutical material, and decay of the batch of radiopharmaceutical material. The example method includes sharing, using the at least one processor, the record with a second copy of the distributed ledger.

BRIEF DESCRIPTION OF THE DRAWINGS

The figures are not scale. Wherever possible, the same reference numbers will be used throughout the drawings and accompanying written description to refer to the same or like parts.

DETAILED DESCRIPTION

Figure 1:
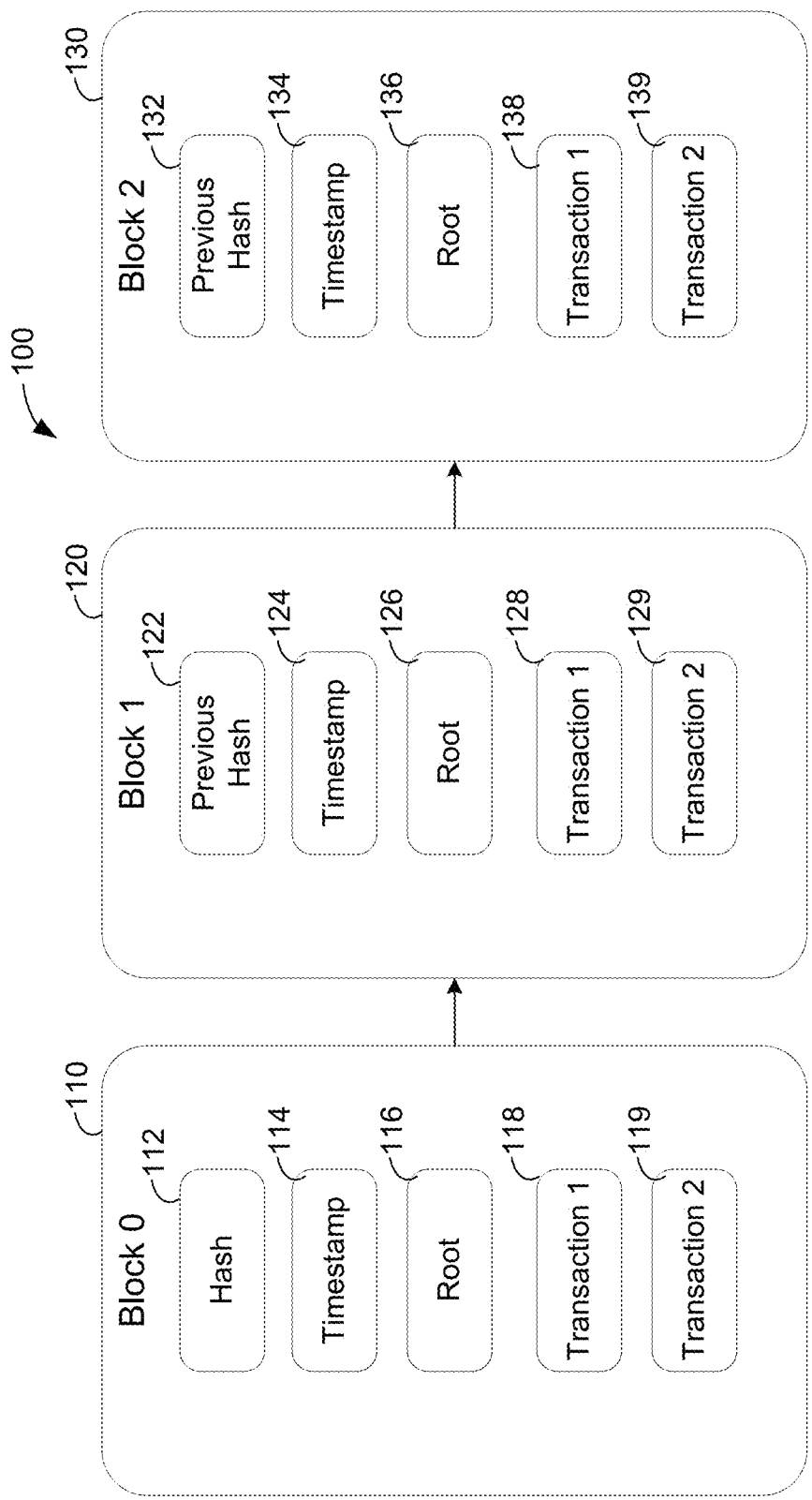
FIG. 1 illustrates an example distributed ledger.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "radioimaging", "radiopharmaceutical", and "radioisotope" are used interchangeably.

While certain examples are described below in the context of medical or healthcare systems, other examples can be implemented outside the medical environment. For example, certain examples can be applied to the handling of non-medical radioactive materials, etc.

I. Overview

Nuclear Imaging

A nuclear medicine imaging exam uses a small amount of a radioactive material (e.g., a radiotracer or radiopharmaceutical) that is injected into the target's bloodstream, inhaled, or swallowed and emits gamma rays that can be detected by an imaging camera (e.g., a gamma camera, etc.) connected to a computer to form images of the target. Nuclear medicine imaging provides unique information that often cannot be obtained using other imaging procedures and offers the potential to identify disease in its earliest stages.

Positron emission tomography (PET) imaging is a nuclear medicine exam that uses a small amount of radioactive drug to show differences between healthy and diseased tissue and form a three-dimensional (3D) image of functional processes in the body of the target. Single-photon emission computed tomography (SPECT) is a nuclear medicine tomographic imaging technique using gamma rays and a gamma camera to capture image data of a target to form a 3D image.

PET and SPECT imaging systems are increasingly used for detection of diseases and are useful in providing early detection and a definite diagnosis for such diseases (e.g., disease states within oncology, cardiology and neurology). For example, currently, a large percentage of PET and SPECT tests are related to cancer detection, evaluations of myocardial perfusion, and early Alzheimer detection. These diseases require early diagnosis to allow a timely and effective treatment.

PET and SPECT imaging systems create images based on the distribution of positron-emitting isotopes and gamma emitting isotopes, respectively, in the tissue of a patient. The isotopes are typically administered to a patient by injection of radiopharmaceuticals including a probe molecule having a positron-emitting isotope, e.g., carbon-11, nitrogen-13, oxygen-15, or fluorine-18, or a gamma radiation emitting isotope, e.g. technetium-99 or iodine-123. The radiopharmaceutical is readily metabolized, localized in the body or chemically binds to receptor sites within the body. Once the radiopharmaceutical localizes at the desired site (e.g., chemically binds to receptor sites), a PET or SPECT image is generated.

Systems such as GE's FASTlab™ and FASTlab™ 2, Drytec™ generator, etc., can be used to make radiotracer material for use in PET, SPECT, and/or other nuclear imaging. Systems such as FASTlab™ use an automated cassette-based system including pre-measured quantities of chemicals involved in radiopharmaceutical synthesis to host reactions which produce radiotracer material (e.g., [18F] Flutemetamol, etc.) over multiple runs. Certain examples integrate reagents to enable performance of multiple runs in the same hot cell (e.g., using Fluorodeoxyglucose (FDG) citrate, etc.). Solid phase extraction, high performance liquid chromatography, etc., can be used to purify the synthesized radiotracer material.

Other examples of radio radiopharmaceuticals include 18F-FLT ([18F]fluorothymidine), 18F-FDDNP (2-(1-{6-[(2-[18F]fluoroethyl)(methyl)amino]2-naphthyl}ethylidene) malonitrile), 18F-FHBG (9-[4-[18F]fluoro-3-(hydroxymethyl)butyl]guanine or [18F]-penciclovir), 18F-FESP ([18F]-fluoroethylspiperone), 18F-p-MPPF (4-(2-methoxyphenyl)-1-[2-(N-2-pyridinyl)-p-[18p]fluorobenzamido]ethylpiperazine) and 18F-FDG ([18F]-2-deoxy-2-fluoro-D-glucose).

Radioactive isotopes in radiopharmaceuticals are isotopes exhibiting radioactive decay, for example, emitting positrons. Such isotopes are typically referred to as radioisotopes or radionuclides. Example radioisotopes include 18F, 124I, 11C, 13N and 15O, which have half-lives of 110 minutes, 4.2 days, 20 minutes, 10 minutes, and 2 minutes, respectively.

PET radiotracers are often produced at a central facility and then distributed to other hospitals or imaging facilities where they are used. It is critical to schedule patient exams and PET tracer production to ensure that sufficient activity is available when the patient is having the imaging exam. Often, the producer (e.g., a PET center) and user (e.g., an imaging facility) are different legal entities, and challenging logistics also involve a time-critical transaction in selling and buying decaying materials whose value is related to its decaying activity, for example.

Because radioisotopes have such short half-lives, the synthesis, purification, storage, transportation, and use of the corresponding radiopharmaceutical must be rapid. For example, many of these processes, such as synthesis, purification, and quality control assessment, should be completed in a time well under the half-life of the radioisotope in the radiopharmaceutical. Accordingly, the time involved in synthesizing, processing, and handling the radioisotope can be a bottleneck to effective use of the radioisotope in nuclear medicine imaging for patient diagnosis to drive patient treatment.

Other radioisotopes are supplied using generators. For example, a supply of Tc-99m can be formed using GE's Drytec™ generator. The generator is shipped from a manufacturing facility containing a specific amount of activity. Generators are supplied cross-country, such as on a weekly basis. Due to the high material value, generators are usually sent back to the manufacturer after the activity supplied has decayed and re-used.

End-users have to pre-order their generator and are not be able to purchase an additional generator ad-hoc outside the distribution and collection schedule. End users also cannot store unused activity beyond the decay time and beyond the time during which the generator is at the user's facility. Therefore, while the user is billed for the entire amount of material, any unused activity is wasted.

Previously, no systematic mechanism existed to enable trading of surplus generator activity between two end-users who may be based close to each other. There was no communication mechanism that, for example, discloses that one user is utilizing their generator less often than planned in a given period while another user is in need of additional activity due to a busier patient schedule, etc. Therefore, activity is unnecessarily lost that could be utilized if the two users were able to exchange generators. Also, some patient exams may not occur when they are needed due to lack of available Tc-99m activity, etc.

Distributed Ledger

A blockchain is a list of records or blocks that are linked and grow to track a history of transactions and/or other evolution of information. The blocks in the blockchain provide a history of the transaction and/or other information state. The blockchain can be public (e.g., readable by anyone) or private (e.g., encrypted to be read only by those with a key). A blockchain and/or other distributed ledger technology can be used as a digital tool to manage physical assets that are traded between many entities. Blockchain and other distributed ledgers provide technological advantages including transparency and traceability of tracking assets and enablement of transactions, for example.

Blockchain technology is a distributed computing mechanism designed to provide a degree of fairness such that one entity is not advantaged while another entity is disadvantaged. A blockchain is a distributed, public ledger of transactions (e.g., financial transactions, data transactions, etc.) in which the transactions are recorded publicly and chronologically and can be verified by participants without a central authority. Blockchain applies cryptographic algorithms to a shared or distributed database to allow any user to read the database, add to the database, and to help ensure no single user can control what is written to the distributed database. Any blockchain user can view all transactions with respect to the distributed database. Blockchain technology provides disintermediation to reduce intermediaries in communication between data producers and data consumers, for example. That is, rather than engaging a middleman to facilitate a transaction, two entities (e.g., a data consumer and a data supplier) can connect and engage in a transaction directly. Other entities can see the transaction, so the blockchain serves as a distributed consensus engine for the entities to verify and/or otherwise agree to the existence of the transaction.

FIG. 1 illustrates an example blockchain 100 including a plurality of records or blocks 110, 120, 130. Each record 110, 120, 130 includes a hash value 112, 122, 132 (e.g., a hash value or other address of a previous block in the chain 100), a timestamp 114, 124, 134 of the record 110, 120, 130, and an address of a root 116, 126, 136 of the blockchain 100. Further, each record 110, 120, 130 includes transactions 118-119, 128-129, 138-139 associated with the respective record 110, 120, 130. Thus, the blockchain 100 is a chain of time-stamped, cryptographically secured, immutable blocks of consensus-validated data. The chain or ledger 100 exists with multiple users, in multiple places, as a series of synchronized copies, for example.

II. Example Nuclear Medicine Product Management Systems and Associated Methods

Certain examples leverage a blockchain and/or other distributed ledger to help manage a perishable good in nuclear medicine imaging, namely a radioisotope, also referred to as a radiotracer or radiopharmaceutical. The radioisotope decays over time, often rapidly, so tracking the usable life of the substance via a blockchain allows a supplier and one or more potential buyers/users to evaluate the viability and usable life of the material until the material is no longer usable for its intended purpose (e.g., PET or SPECT imaging, etc.).

In certain examples, units of radioactivity are linked to a digital unit managed by blockchain technology. Radioactivity can be represented as a perishable crypto-currency whose units need to be spent within their finite lifetime. The visibility of the units of this perishable currency that are in circulation via the blockchain allows real-time trading and efficient utilization of the currency. Producers of radioactivity (e.g., PET centers synthesizing tracers, manufacturers of generators, etc.) issue new "currency" and bring the supply into circulation. Users, such as hospitals, clinics, imaging centers, etc., are buyers which analyze and add to the chain of records of radiopharmaceutical use and usable life remaining for the product. Product half-life, availability, and time, date, and place of use can be tracked and managed via the blockchain (e.g., blockchain 100) to help ensure maximum use of the available material, quality control of the product, and improved management of the nuclear imaging supply chain, for example.

In certain examples, a radiopharmaceutical generator supply chain (e.g., GE Drytec™, etc.) can be managed via the blockchain 100 to provide full traceability of each generator in an organization, the activity contained therein, and location of generators, product, and activity. In addition to the benefits of a fully traceable system, the distributed ledger also provides more transparency to end-users. Furthermore, the distributed ledger of the blockchain 100 enables users to trade activity between each other. For example, if one hospital does not use its generator fully during a given week, that hospital could trade use of the generator to another hospital nearby who has more nuclear medicine exams scheduled in the same week and desires additional generator activity but cannot otherwise obtain an additional generator from a producer (e.g., General Electric Company, etc.). This transaction between two end-users, stored in the blockchain 100, is also be visible to the producer, which in turn facilitates collection and recycling of generators regardless of whether the generator has changed location since being shipped to a particular customer. Thus, the producer knows that the generator has been moved from hospital A to hospital B and can request and/or expect return of the generator from hospital B, for example. As such, the blockchain 100 combines tracking and tracing capabilities with an additional ability to exchange activity between users. The blockchain 100 can also facilitate billing of users according to the activity that they have actually utilized, rather than charging a per-generator price, which disadvantages user A who will only partially use the activity provided.

In another example, PET tracer manufacturing can be managed via the blockchain 100. The distributed ledger enables full visibility of tracer location (e.g., a location at which batch of GE's Vizamyl™ tracer is produced, etc.), how much activity the batch of tracer has, how the tracer batch may be dispensed into a number of doses, and how these doses would be used, for example. Leveraging the blockchain can facilitate improved utilization of tracer product among end-users by allowing surplus doses from a batch at a PET center to be shipped to other places nearly where demand exists. For example, the blockchain can track a shipment from a producer to a first PET center, which then sells a remaining portion of the tracer shipment to a second PET center. Imaging facilities requiring additional doses of specific PET tracers can obtain timely information about PET tracer production by having access to the blockchain 100, for example. A PET production facility can be in a position to gauge demand via the blockchain 100, for example.

In certain examples, a distributed ledger or blockchain can be constructed and/or expanded by a generator or synthesizer producing radiopharmaceutical material. For example, GE's FASTlab™ platform can include a processor and network connection to process radioactivity measurements upon a release of a batch of radiotracer material (e.g., PET tracer, etc.). When a batch of material is generated and released by the synthesizer, a record or block is created in the chain representing a unit or usable quantity of the material. The record can include a measure of the quantity of the material and a timestamp for creation of the material. The timestamp enables tracking or monitoring of the usable life of the material as it begins to decay. By tracking quantity, time, and composition of the material, decay and remaining usable life for the quantity of material can be determined and dynamically updated as time passes. The local system can generate a record that is shared with a remote system (e.g., a cloud-based server, central server, customer system, etc.) to propagate the ledger and new record, for example. Thus, a customer system can view the record, purchase the material, track the record and passage of time, and provide a new record as the material is used (e.g., using a portion of the material and selling a viable remainder to a secondary customer, etc.).

Figure 2:
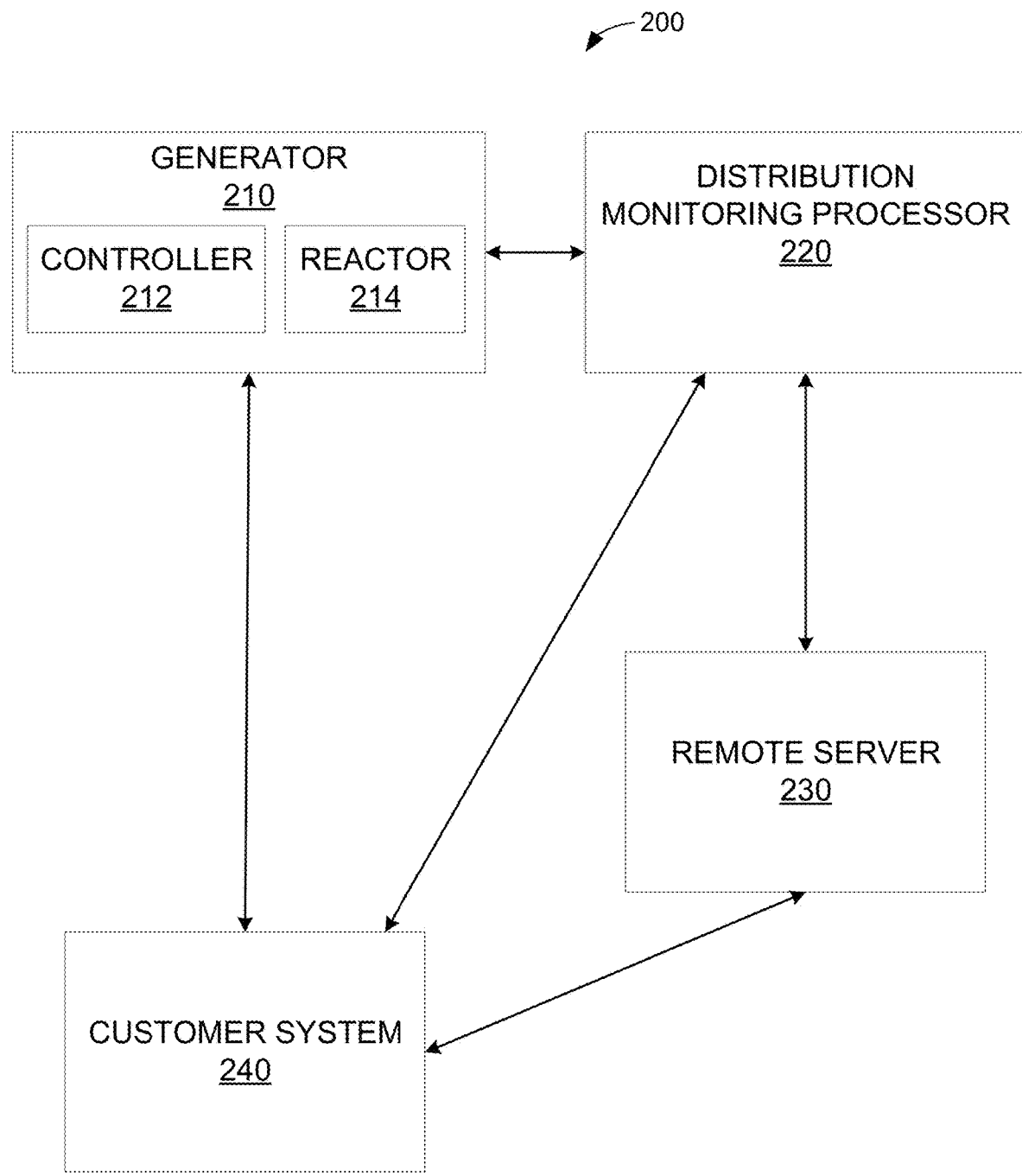
FIG. 2 illustrates an example apparatus including a generator to produce radiopharmaceutical material and a distribution monitoring processor to generate records for production of the radiopharmaceutical material and track its usage and useful life.

FIG. 2 illustrates an example apparatus or system 200 including a generator 210 to produce radiopharmaceutical material and a distribution monitoring processor 220 to generate records for production of the radiopharmaceutical material and track its usage and useful life. The distribution monitoring processor 220 is connected to a controller 212 in the generator 210 to receive an indication of a quantity of radioisotope material synthesized in a cassette or other reactor 214 of the generator 210. The distribution monitoring processor 220 generates a record in a distributed ledger (e.g., a blockchain, a hashgraph, a directed acyclic graph, etc.) corresponding to the produced material (e.g., a type, quantity, starting timestamp, location, etc.). The distribution monitoring processor 220 can relay the distributed ledger record and/or an update to the ledger to a remote server 230 (e.g., a cloud-based server and/or other remote server run by a provider of the generator 210, a third party service provider, a clearing house or broker for the material, etc.). The remote server 230 can work with the distribution monitoring processor 220 to verify the distributed ledger, facilitate exchange of messages, connect potential users/buyers with the material at its current location, etc.

The material and/or information regarding the material can be provided to a customer subsystem 240 which uses the material and updates the associated record and/or adds a new record to the distributed ledger indicating its use of a portion of the material. The records in the distributed ledger can be used to monitor usable life of the material, facilitate contracts and/or other agreement for sale of all or part of the material.

Figure 3:
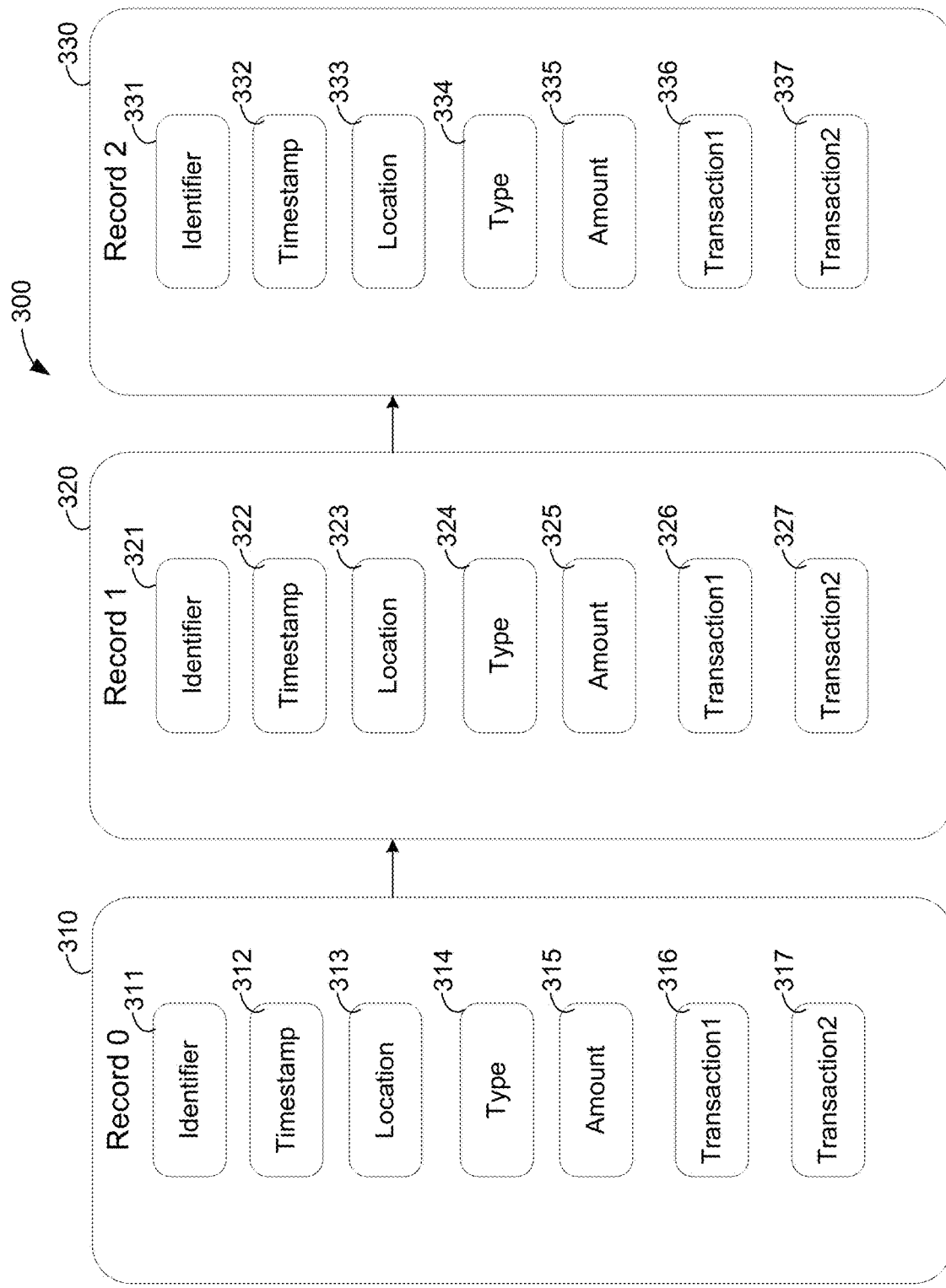
FIG. 3 illustrates an example distributed ledger including records corresponding to batches of a radioimaging agent produced by the generator of FIG. 2.

FIG. 3 illustrates an example distributed ledger 300, similar to the example blockchain 100, including records 310, 320, 330 corresponding to batches of a radioimaging agent produced by the generator 210. For example, the ledger 300 can be an implementation of the blockchain 100 customized for the records 310-330 of radiopharmaceutical material or the ledger 300 can be an alternate form of distributed ledger to track amount, location, decay, etc., of the radiopharmaceutical material.

As shown in the example ledger 300 of FIG. 3, a record 310 is created by the processor 220 when a batch of radiopharmaceutical material is synthesized by the generator 210. The example record 310 includes an identifier 311 associated with the record 310, a timestamp 312 corresponding to the synthesis of the material by the generator 210, a location 313 of the generator 210, a type 314 of the radiopharmaceutical material, and an amount 315 of the material. Using the type 314, amount 315, and timestamp 312, a remaining usable life of the material can be determined given a half-life associated with the type 314, starting with the amount 315 at the time of the timestamp 312. The distribution monitoring processor 220 can track degradation of the material associated with the record 310 as time elapses and can provide this information to the remote server 230 and/or the customer system 240, for example. Additional records 320, 330 in the distributed ledger 300 can be for the same and/or different batches of material. Thus, additional material produced by the same or a different generator 210 can be associated with a subsequent record 320, 330 and have an associated identifier 321, 331, timestamp 322, 332, location 323, 333, type 324, 334, amount 325, 335, etc.

In certain examples, a subsequent record 320 can be for the same batch of material as the first record 310 after a certain amount of the material has been used. The record 320 can show a remaining amount 325, different from the initial amount 315, and the usable life of the remaining amount 325 can be tracked using the timestamp 322, type 332, etc. Activities such as transportation time, sharing/use of material, etc., are updated in the ledger 300 by the processor 220 and/or remote server 230 and factor into a decay calculation to determine a remaining usable life for the quantity 325 of the remaining material, for example.

In certain examples, once all of the material is used and/or a usable life of the material is exhausted, the associated record 310, 320, 330 can be removed from the ledger 300. In other examples, the amount 315-335 of the material is reduced to zero but the record 310-330 maintained in the ledger 300 for historical tracking and/or auditing purposes, etc. In certain examples, the records 310-330 include an additional field indicating whether or not usable/viable material remains from the associated batch. Thus, records 310-330 in which the field does not indicate usable/viable material remaining can be ignored by the processor 220, server 230, and/or customer system 240 when tracking, trading/selling/buying, and/or otherwise managing available material inventory, for example.

In certain examples, each time a transaction occurs to sell or resell all or a portion of the radiopharmaceutical material, a new record 310-330 is created in the ledger 300 to track that material. In other examples, such as shown in FIG. 3, transactions 316-337 occurring with respect to the records 310-330 of radiopharmaceutical material are stored in or with respect to each block or record 310-330 in the ledger 300. For example, a first transaction 316 can include selling the generated material from a producer lab to a first hospital. A second transaction 317 can include reselling a portion of the material from the first hospital to a second hospital. Similar transactions 326-327, 336-337 can be recorded for each record 310-330 in the ledger 300.

Thus, with radioactive material used in nuclear medicine, the material is associated with a known, short decay time for the radioisotopes. Additionally, some of the radioisotopes may be attached to molecules which make the radioisotopes good imaging agents. However, these radioisotopes have a limited lifetime and are to be used before they decay away. During the useful life of the radioisotope material, its activity diminishes (e.g., from 100 hours to 50 hours to 25 hours, etc.) which results in diminishing in strength. Diminished strength results in diminished effectiveness in PET, SPECT, and/or other nuclear imaging until the remaining material is not sufficient to obtain diagnostic quality images of a target. As a result, the value of the radioisotope material decreases as the material ages. For example, an initial batch may be sufficient to dose multiple patients. However, soon the material is only strong enough to dose one patient, and then the material decays such that it is insufficient to dose anyone. The records 310-330 of the distributed ledger 300 allow the distribution monitoring processor 220, the customer subsystem 240, and/or the remote server 230 to monitor material activity including how much material is produced, how much material is dispensed, how much material is left, where the material is located, and how strong the material remains. The information is shared and used for calculations, estimations, and contracts/subcontracts for sale of the material, etc.

In certain examples, the remote server 230 and/or the customer subsystem 240 provide an interface, in conjunction with the distribution monitoring processor 220, so that a user/customer for the radiopharmaceutical material (e.g., a hospital, radiopharmacy, clinic, imaging center, etc.) can see available material within a transportation/delivery radius that allows the material to be transported to their location with usable life remaining for one or more desired imaging tasks. In certain examples, the user/customer can rent the generator 210 to produce the material locally and can then pass the generator 210 on to another customer and/or share the material generated with another customer site, etc. The distributed ledger 300 and coordination between monitoring processor 220 and customer 240 systems (e.g., via the remote server 230) allows precultured and/or other radiopharmaceutical materials to be synthesized, distributed, and redistributed in a decentralized fashion while information regarding the material and associated transactions is maintained for all participants to see and supplement in the records 310-330 of the distributed ledger 300. When a batch of material has been depleted, its record 310-330 can be removed from the ledger 300 and/or marked as exhausted, used, inactive, etc.

In certain examples, a user can submit a request for a certain radioactivity and make an agreement for a generator 210 and/or material through a contract facilitate and represented by the distributed ledger 300 (e.g., via the remote server 230 and/or the distribution monitoring processor 220. In certain examples, a request remains in the ledger 300 and/or on an interface until the request is filled. In certain examples, supplier A may have a desired amount at a first price at a first distance, and supplier B has the desired amount at a second price at a second distance that is father away from the requested user than the first distance. Thus, the amount of usable material from supplier B will be less than the desired amount once the material reaches the requested user, since supplier B is located farther away. Distance, half-life, amount, and cost can be factored in to determining a best supplier for a requesting user.

In some examples, a smart contract facilitated by the distributed ledger 300 of the distribution monitoring processor 220 can reduce its price as decay of the material progresses. That is, the smart contract provides a decaying price for a decaying product.

In certain examples, a cassette and/or kit is provided to make agent A or agent B based on the same radioisotope but different organic molecules. For example, the cassette is barcoded for a particular agent to tell the generator 210, such as GE FASTlab™, etc., which agent to make. The generator 210 runs through a programmed sequence to make the agent in the reactor 214. The controller 212 can calibrate sensors to measure radioactivity going through the generator 210, for example. Demand can be communicated from an end user, such as one or more hospital(s) and/or other healthcare facilities associated with a PET center having the generator 210 and can be correlated with and/or based on a schedule of patients and doses needed for imaging of those patients. The distribution monitoring processor 220 can work with the generator 210 and the customer's subsystem 240 to form a worklist for the radiopharmacy to produce one batch of agent A on Monday, two batches of agent B on Tuesday, etc. Scheduling of radioisotope generation and distribution can be automated including demand and associated requests to configure and drive the generator 210 and delivery and tracking to customers, for example. Timely communication, improved tracking, added capability for management and distribution, and improved use can be achieved, for example.

Rather than manually guess or estimate regarding times, transit, and decay, the monitoring processor 220 can be connected to and/or otherwise in communication with the generator 210 to identify the batch of material, create a record for the material, and track the material through its usable lifespan. In certain examples, once the material is exhausted and/or otherwise unusable, the record can be deleted or inactivated, thereby reducing expansion of the distributed ledger 300 beyond a size that is able to easily be shared between the distribution monitoring processor 220, the remote server 230, and other customer systems 240, etc.

Figure 4:
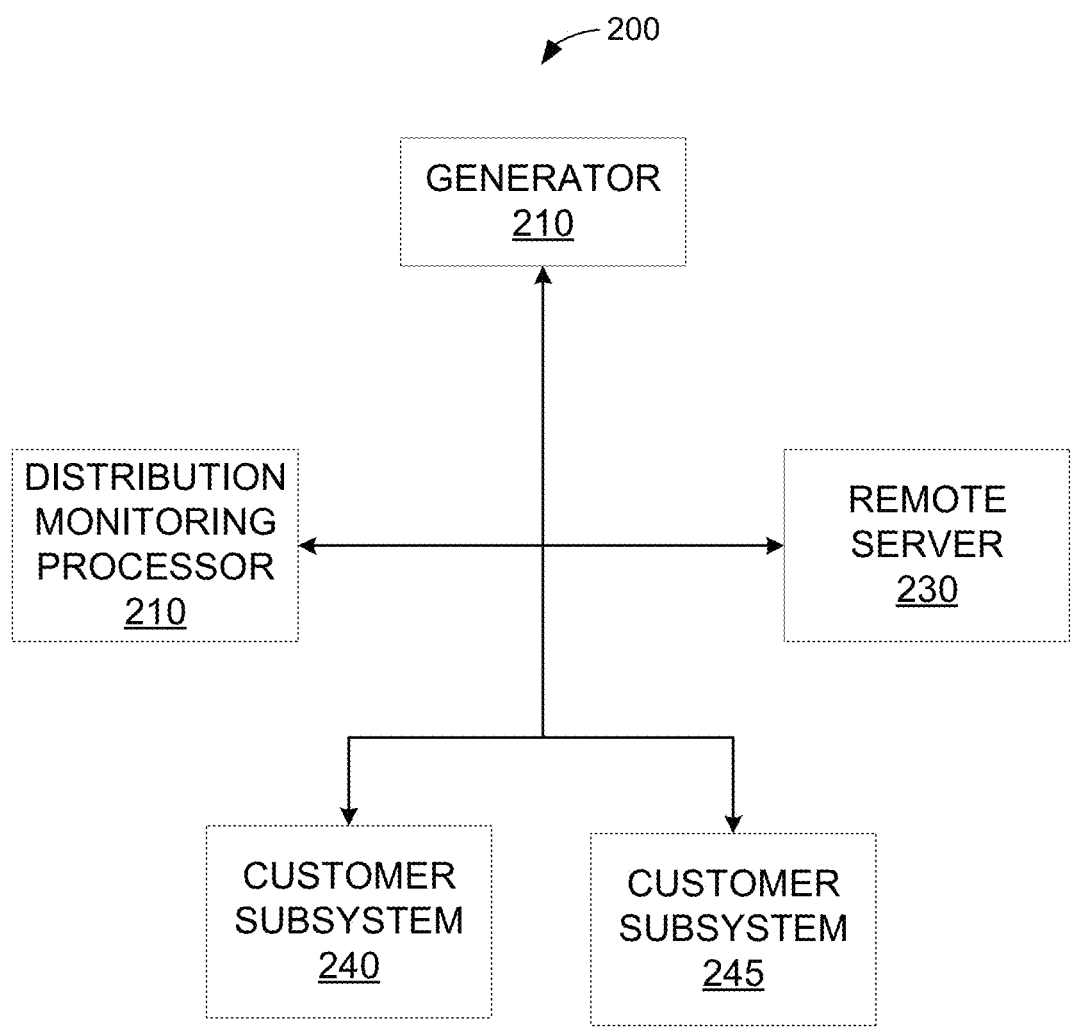
FIG. 4 illustrates an example implementation of the system of FIG. 2 including a plurality of customer subsystems in communication with the distribution monitoring processor, the remote server, and the generator of the example of FIG. 2.

FIG. 4 illustrates an example implementation of the system 200 including a plurality of customer subsystems 240, 245 in communication with the distribution monitoring processor 220, the remote server 230, and the generator 210. As shown in the example of FIG. 4, the first customer subsystem 240 can be associated with a first customer purchasing material from the generator 210. The synthesis, purchase, and/or shipment of the batch of material from the generator 210 to the customer can trigger the distribution monitoring processor 220 to create a record 310-330 for the batch of material and begin tracking its decay. The processor 220 can provide a copy of the ledger 300 including its updated record(s) 310-330 to the remote/central server 230 and the customer subsystem 240.

After using a portion of the material, the first customer can advertise the remaining material for (re)sale (e.g., from the customer subsystem 240 via the processor 220 and/or the remote server 230, etc.). A second customer can view the ledger 300 and determine to purchase some or all of the remaining material from the batch purchased by the first customer. The second customer subsystem 245 can engage in a transaction with the first customer subsystem 240 to purchase material, and a new record 310-330 can be generated and/or an existing record 310-330 updated in the ledger to reflect the transaction/transfer. The customer subsystems 240, 245 show a record 310-330 of the transaction in the ledger 300, and the processor 220 and remote server 230 also receive the updated ledger 300 indicating the transaction. Monitoring of the usable life of any remaining material can continue until all usable material is exhausted and/or otherwise rendered unusable (e.g., by decay, too small quantity, etc.).

In certain examples, using the ledger 300, a plurality of small quantities of material can be combined by customers into a larger usable quantity of material when the quantity drops below a usable threshold but the material still has usable life remaining. For example, remaining material may still be viable but is now in too small a quantity to satisfy PET, SPECT, and/or other nuclear imaging requirements at a customer. The processor 220 and/or remote server 230 can communicate with customer subsystems 240, 245 to identify multiple smaller remaining batches of material to combine the material into a single usable batch for (re)sale, for example.

Figure 5:
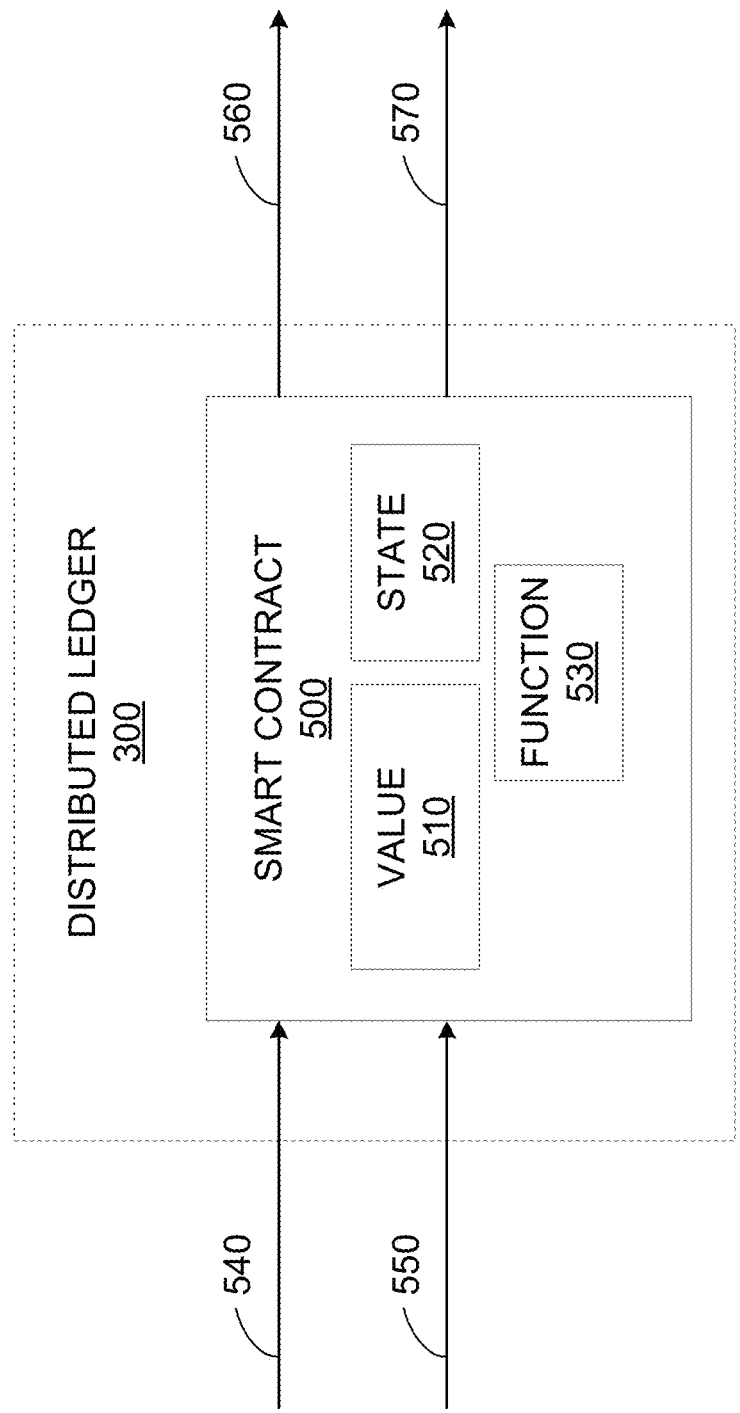
FIG. 5 illustrates an example smart contract for purchase of radioimaging material tracked by the distributed ledger

FIG. 5 illustrates an example smart contract 500 for purchase of radioimaging material synthesized by the generator 210 and tracked by the distributed ledger 300. The example smart contract 500 can be stored as a record 310-330 in the ledger by the distribution monitoring processor 220, the remote server 230, the customer subsystem(s) 240, 245, etc. As shown in the example of FIG. 5, the contract 500 includes a value 510 (e.g., a quantity of material, a cost, etc.) and a state 520 (e.g., available, completed, executed, in execution, delivered, material remaining, etc.). The contract 500 can also include one or more functions 530 executable with respect to the contract 500. Thus, the contract 500 can specify its terms 510 and a status 520 of the execution of those terms using one or more functions 530, for example. For example, functions 530 can include request, product, purchase, shipped, received, resell, return generator, kill, etc. The contract record 500 can receive transaction information 540 and event information 550 and also provide transaction information 560 and event information 570 to another record 310-330 in the ledger 300 and/or system such as the distribution monitoring processor 220, the remote server 230, the customer subsystem 240, 245, etc.

For example, a transaction 540 can provide value 510 to the contract 500 such as through a quantity of material to be purchased and/or other term/condition to the contract 500. An event 550 can impact a state 520 of the contract 500 such as a timestamp of creation of the material, a time of delivery of the material, an identification of type, half-life, etc., of the material, etc. As material purchased under the contract 500 is used and/or decays, transaction information 560 and event information 570 can be propagated to another record 310-330 and/or another system 220-240. For example, usage of material and/or passage of time, etc., can be an event 570 impacting this and/or another contract 500 or record 310-330, etc. An agreement to sell a remaining portion of unused yet usable material can be a transaction 560 impacting this contract 500 and spawning another contract 500 and/or associated record 310-330, etc. Thus, the smart contract 500 can be used to track sale, rental, and/or other transaction involving the generator 210, radioisotope material, associated services, etc., and the smart contract 500 can automatically change as the material (and/or the generator 210) is used, decays, is resold, etc.

The smart contract 500 can be implemented as computer program code that can be executed to enable/facilitate performance of the contract/agreement between parties (e.g., between the generator 210 and customer(s), etc.) using the ledger 300. Conditions and/or updates to the contract can be implemented as processor-executable instructions executed by the processor 220 and/or another processor to implement and/or track execution of the contract 500. For example, monitoring of usable life remaining in a batch of sold material (e.g., based on a half-life associated with a type of the material and a starting/generation time of that material, etc.) can be calculated by the smart contract 500 which then updates and/or creates a new record 310-330 associated with the batch of material in the ledger 300 to reflect updated information regarding remaining material and its usable life. Terms of the contract 500 can be coded as logic statements governing conditions and results of the contract 500 and associated material. The contract 500 can be fully automated to execute on its own with respect to the distributed ledger 300 and/or can be executable by the processor 220, remote server 230, customer subsystem 240-245, etc., to fulfill the contract 500, for example. Thus, the contract 500 can be formulated entirely in executable code and/or can include additional elements to be interpreted by a processor, for example. The contract 500 can be executed within the ledger 300 (e.g., code forming the contract 500 is coded into blocks of the blockchain and/or other distributed ledger 300, etc.) and/or executed outside the ledger 300 and provides information (e.g., new and/or updated records 310-330, etc.) back to the ledger 300, for example. In certain examples, anyone can add a contract 500 and/or make changes to records 310-330 in the ledger 300. In other examples, access to the ledger 300 and associated records 310-330, contracts 500, etc., is restricted such as based on processor authorization (e.g., authorized nodes), user authorization, etc.

Figure 6:
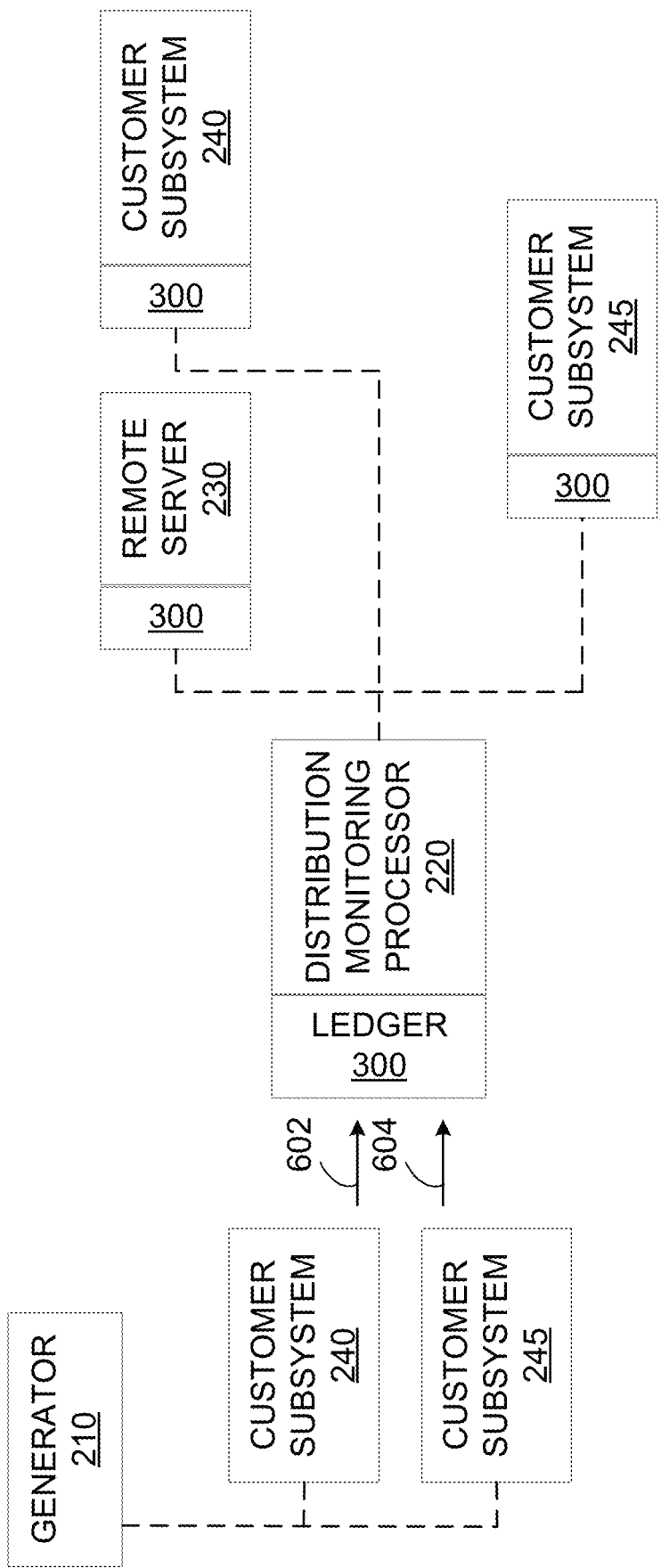
FIG. 6 shows an example peer-updated system in which the generator of FIG. 2 provides material to be purchased and used by customers, and transactions are performed with customer subsystems to sell material to the respective customer.

FIG. 6 shows an example peer-updated system 600 in which the generator 210 provides material to be purchased and used by customers, and transactions 602, 604 are performed with customer subsystems 240, 245 to sell material to the respective customer. Such transactions are noted as records 310-330 in the distributed ledger 300 by the distribution monitoring processor 220, and the transactions 602, 604 and/or a copy of the records 310-330 are reflected in the ledgers 300 maintained by the remote server 230, and customer subsystems 240, 245, as well as the processor 220. Thus, addition, subtraction, exchange, resale, and/or other transaction involving material from the generator 210 (and/or use of the generator 210 itself, etc.) is reflected in records 310-330 of the ledger 300 and can be verified by peer systems 220-245 to confirm accuracy and validity of the transactions, usable life and amount of material remaining, associated timing, etc. Thus, for each smart contract 500 transaction 602, 604, peer systems with copies of the ledger 300 can verify the contract 500 (e.g., can verify the type, half-life, and remaining usable life of the material), can track chain of custody of material and/or its generator 210, can dynamically determine allocation and verify allocation of material and/or the generator 210, etc. Thus, peer systems can provide feedback regarding record content, record updates, and transactions involving records, etc.

Thus, suppliers and users know how much material is being generated and how the material (and the generator) is being used. In certain examples, the generator 210 is a non-perishable, non-sellable device that is loaned to a customer and then returned to the supplier to generate more product. If customer A sells to customer B, the supplier would not be aware and would be unable to track without the distributed ledger 300, for example. Smart contracts can be created and/or updated, locations can be monitored, pickup can be scheduled, usage can be tracked, etc., via the distributed ledger 300. Smart contracts 500 can calculate delay, estimate shipping/delivery time, schedule pickup, determine and calculate a best supplier to provide a purchaser with what they need at the right time, etc., as encoded in the smart contract 500. In certain examples Internet of Things (IoT) devices can automatically measure material during production and retrieval in real time (and/or substantially real time given transmission and data processing latency) to provide to the ledger 300.

In certain examples, price can be monitored, recorded, and controlled via the distributed ledger 300. For example, price boundaries and/or other restrictions can be placed on transactions for material and/or generator 210 resources via the ledger 300. In certain examples, an auction and/or reverse auction can be facilitated for sale of material, generator 210, etc., via records 310-330 of the distributed ledger 300. Such transactions can occur quickly via the blockchain 300 while the material is still viable, and systematic reselling can be facilitated at a price determined by market forces, for example.

In certain examples, smart contracts 500 facilitate a radiopharmaceutical generation and exchange process flow. For example, a user invokes a purchase radiopharmaceuticals smart contract, such as a Flutemetamol (18F) tracer dose request, and provides parameters 510 to initiate the contract 500. Such parameters can include an initiator public key to identify the initiator of the contract 500 as well as other parameter information 510 such as tracer type, quantity, address of requestor, delivery method, etc. The smart contract 500 includes a function call 530 for each step or action in the process.

For example, after initiating a request for the smart contract 500 using the public key of the initiator, the user then calls the request function 530 of the smart contract 500 with parameters. The request function 530 puts a request transaction into the blockchain or other distributed ledger 300. This transaction includes information for labs to evaluate the request. Labs that would like to fulfill this request would invoke a produce function 530 of the smart contract 500. An address of the smart contract 500 is in the request transaction, for example.

In certain examples, the same instance of the smart contract 500 is used for all transactions. Multiple labs can respond to the request transaction by invoking the produce function 530 of the smart contract 500. For each lab that invokes the produce function 530, a transaction 316-337 is added to a block 310-330 in the blockchain 300. The initiator of the contract 500 can evaluate all produce transactions 316-337 and select a producer for their needed tracer from any of the produce transactions 316-337.

The initiator of the contract 500 can then invoke the purchase function 530 of the smart contract 500, which, in turn, puts a purchase transaction 316-337 into a block 310-330 on the blockchain 300 and also sends the purchase information to a selected lab. This invocation also disables the produce function 530 of the smart contract 500, signaling that that this contract 500 has a lab filling the request. If multiple produce transactions 316-337 were received, the smart contract 500 notifies other labs that their produce transaction was not selected.

The lab awarded the contract then produces the tracer and delivers the tracer to the lab under the terms of the smart contract 500. When produced, the lab invokes the deliver function 530 of the smart contact 500, which in turn would place the deliver transaction 316-337 in a block 310-330 on the blockchain 300 and also send the information directly to the lab.

When the initiator receives the tracer, the received function 530 of the smart contract 500 is invoked, and the transaction 316-337 is added to a block 310-330 of the blockchain 300 and also sent directly to the lab. If all terms of the smart contract 500 have been met by both sides, the smart contract 500 is closed and added to the blockchain 300 as a transaction 316-337. If any condition(s) are not met, the smart contract 500 invokes penalties and/or other ramifications specified in the smart contract 500. Penalties can also be placed on the initiator if payment and/or other terms of the smart contract 500 were not met by the initiator. The smart contract 500 is closed out and added to a block 310-330 on the blockchain 300 when all terms of the contract 500 have been fulfilled, and the instance of the smart contract 500 is removed from the system (e.g., the invoked instance of the smart contract 500 is deleted, rather than the entire blockchain 300).

At any given time, there can be multiple instances of invoked smart contracts 500 in the system placing transactions 316-337 in blocks 310-330 of the blockchain 300. In certain examples, each instance is a request for a tracer and follows the flow as specified above.

The above workflow is an example for PET tracers with short half-lives, such as 110 minutes—these are very time-critical workflows. For other tracers, such as "99mTc generators" that are shipped in generators with parent half-lives of 66 hours, the workflow is not as time critical. Therefore, a different smart contract 500 can be used.

For example, a user invokes a sell radiopharmaceuticals smart contract 500 with parameters 510 to initiate the contract 500. Example parameters 510 include the seller's public key that identifies the initiator as well as other information such as tracer type, quantity, address, delivery method, etc. This smart contract 500 also includes a function call 530 for each step or action in the process. For example, after initiating a sell radiopharmaceutical smart contract 500 with the public key of the initiator, the initiator then calls the sell function 530 of the smart contract 500 with associated parameters 510. The sell function 530 can add details of the tracer sell transaction 316-337 into the blockchain 300. This transaction 316-337 includes information for prospective buyers to evaluate the offer. The address of the smart contract 500 is in the sell transaction 316-337 and the same instance of the smart contract 500 is used for all transactions, for example.

When a lab, or buyer would like to buy the tracer, they invoke the purchase function 530 within the smart contract 500. That transaction 316-337 is added to a block 310-330 in the block chain 300. The initiator (producer) of the contract 300 then invokes the produce function 530 of the smart contract 500 to produce the tracer or may go directly to the shipped function if the tracer is already in stock. The appropriate (produce or shipped) transaction 316-337 is placed into a block 310-330 on the blockchain 300 and shipping information is sent to the lab once the tracer is shipped.

When the buyer receives the tracer, the received function 530 of the smart contract 500 is invoked, and the transaction 316-337 is added to a block 310-330 and additionally sent directly to the lab. In this use case example, the tracer is shopped in a generator containing a parent material. The buyer generates the actual dose from the parent material in the generator. This allows for multiple doses and is also conducive to reselling due to the longer half-life of the parent.

The original (or subsequent buyers) can resell the generator or retain the generator. Once the parent material is no longer viable (or at any time), the current purchaser of the tracer can invoke the return generator function 530 of the smart contract 500.

When the producer receives the returned generator, the contract 500 is complete. If all terms of the smart contract 500 have been met by all parties, the smart contract itself 500 is to be closed out and added to the block chain 300 as a transaction 316-337. If any conditions are not met, the smart contract 500 invokes penalties and/or other ramifications specified in the smart contract 500. Penalties can also be placed on either party if payment or other terms of the smart contract 500 are not met.

The smart contract 500 is closed out and added to a block or record 310-330 on the blockchain or other distributed ledger 300 as a transaction 316-337 when all terms of the contract 500 have been fulfilled and the instance of the smart contract 500 is removed from the system (not the blockchain 300, just the invoked instance of the smart contract 500 is deleted). In certain examples, the resell, purchased, shipped, and received functions of all smart contracts 500 can be invoke multiple times in the life of the contract 500 if re-selling occurs.

Figure 7:
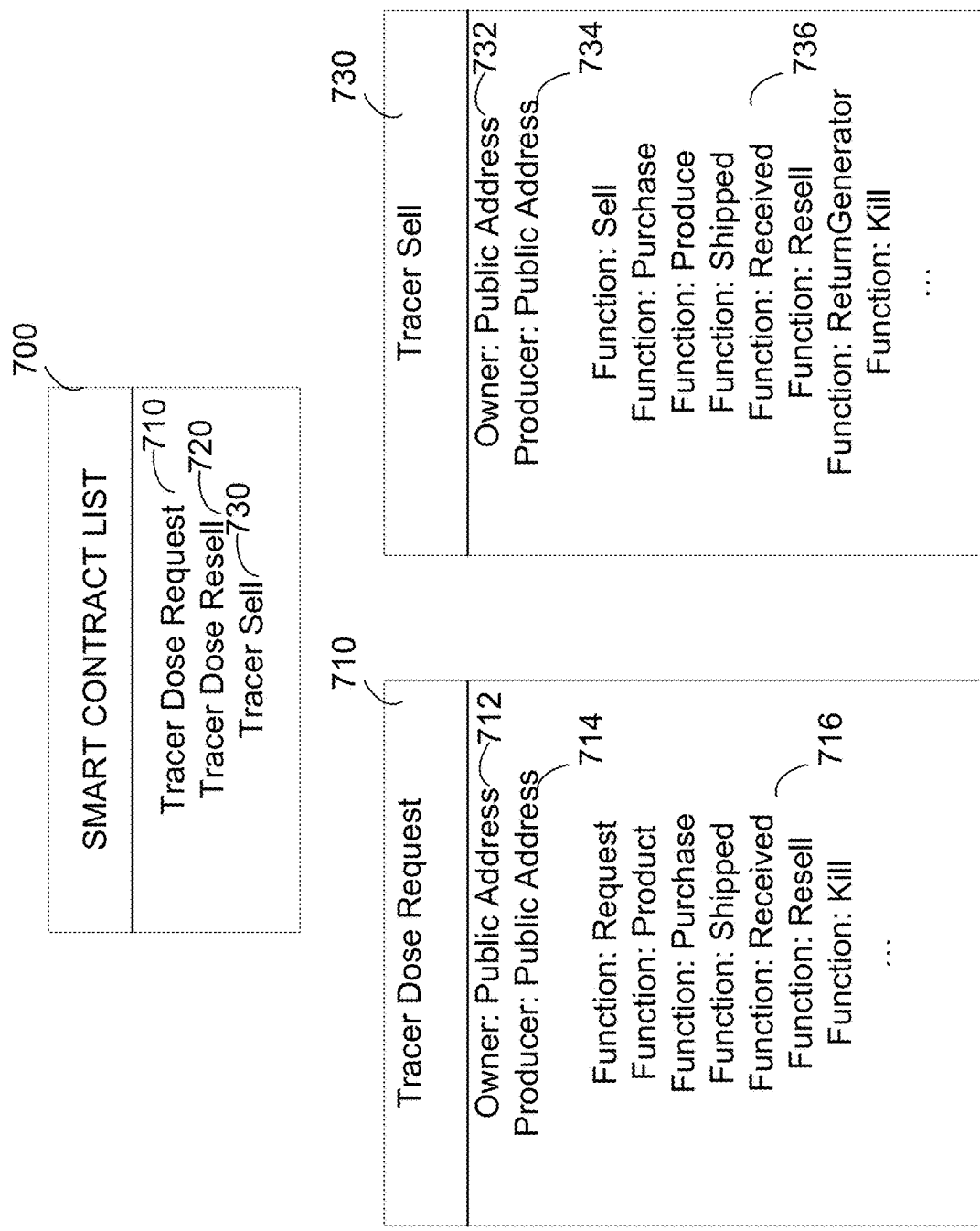
FIG. 7 illustrates an example set of smart contracts.

FIG. 7 illustrates an example set 700 of smart contracts 710-730. Each contract 710-730 in the list 700 includes a model of information such as an owner 712-732, a producer 714-734, and one or more functions 716-736 executable with respect to the smart contract 710-730. Thus, the model/data structure for each smart contract 710-730 defines its owner 712-732, its associated producer 714-734, and one or more functions 716-736 that can be executed by entities with respect to the contract 710-730, for example. For example, FIG. 7 shows a tracer dose request contract 710, which defines the contract owner 712, the tracer dose producer 714, and provides a plurality of functions 716 executable with respect to the smart contract 710 including request (e.g., request tracer dose), produce (e.g., produce tracer dose), purchase (e.g., purchase tracer dose), shipped (e.g., tracer dose has shipped), received (e.g., tracer dose has been received), resell (e.g., tracer dose available to be resold), kill (e.g., terminate the order/usage, remove the contract instance), etc.

The example of FIG. 7 also shows a tracer doss sell contract 730, which defines the contract owner 732, the tracer dose producer 734, and provides a plurality of functions 736 executable with respect to the smart contract 730 which includes request (e.g., request tracer dose), produce (e.g., produce tracer dose), purchase (e.g., purchase tracer dose), shipped (e.g., tracer dose has shipped), received (e.g., tracer dose has been received), resell (e.g., tracer dose available to be resold), kill (e.g., terminate the order/usage, remove the contract instance), etc.

Figure 8:
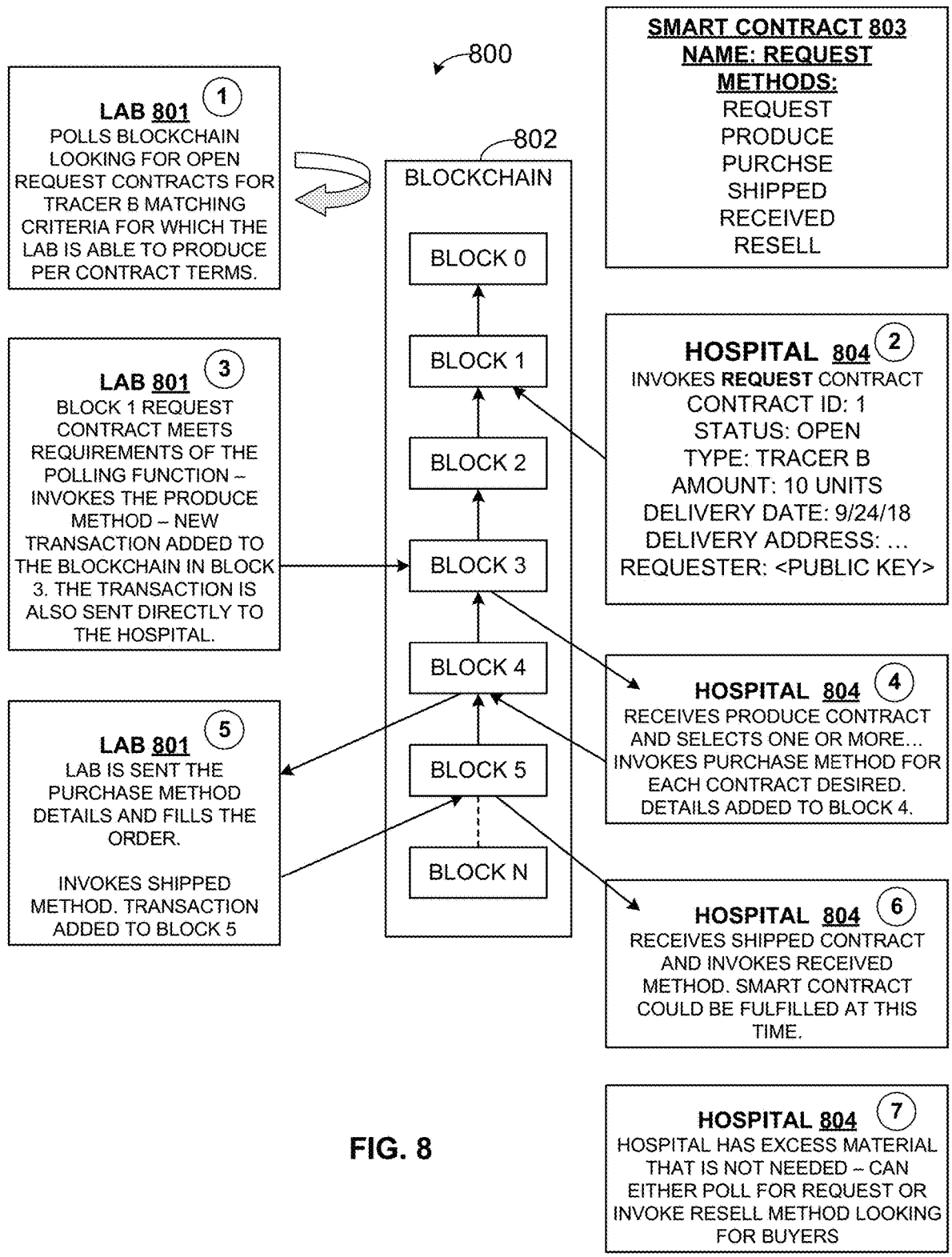
FIG. 8 shows an example transaction flow for an example radiopharmaceutical blockchain.

FIG. 8 shows an example transaction flow 800 for an example radiopharmaceutical blockchain 802 (e.g., implementing the example distributed ledger 300 of FIG. 3). As shown in the example of FIG. 8, at 1, a first lab 801 polls the blockchain 802 looking for open request contracts for Tracer B matching criterion for which the lab 801 is able to produce according to terms of a smart contract 803. At 2, a hospital 804 invokes the request smart contract 803. The invocation of the smart contract 803 is stored as a transaction in block 1 of the blockchain 802.

At 3, the block 1 request contract 803 is determined to meet requirements of a polling function, and the lab 801 invokes a produce function of the smart contract 803. The invocation of the produce function is added as a transaction to the blockchain 802 at Block 3. Information regarding the transaction can also be sent directly to a system at the hospital 804.

At 4, the hospital 804 receives the produce contract 803 and selects one or more Tracer B order quantities. A purchase method of the contract 803 is invoked for each contract 803 desired, and contract 803 details are added to Block 4 of the blockchain 802, which also notifies the lab 801 of the purchase.

At 5, the lab 801 is sent details of the purchase method of the contract 803 and fills the order for the quantity(-ies) of the Tracer B. The lab 801 invokes the shipped method of the smart contract 803, and the transaction is added to Block 5 of the blockchain 802. The hospital 804 system is also notified of the transaction. At 6, the hospital 804 receives the shipped contract and invokes a received method of the contract 803. The smart contract 803 can be fulfilled based on receipt of the material at the hospital 804, for example.

At 7, the hospital 804 has excess material that is not needed. The hospital system 804 can poll for a request and/or invoke a resell method of the smart contract 803 to look for potential buyers of the excess material, for example.

While example implementations are illustrated in conjunction with FIGS. 1-8, elements, processes and/or devices illustrated in conjunction with FIGS. 1-8 may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 9:
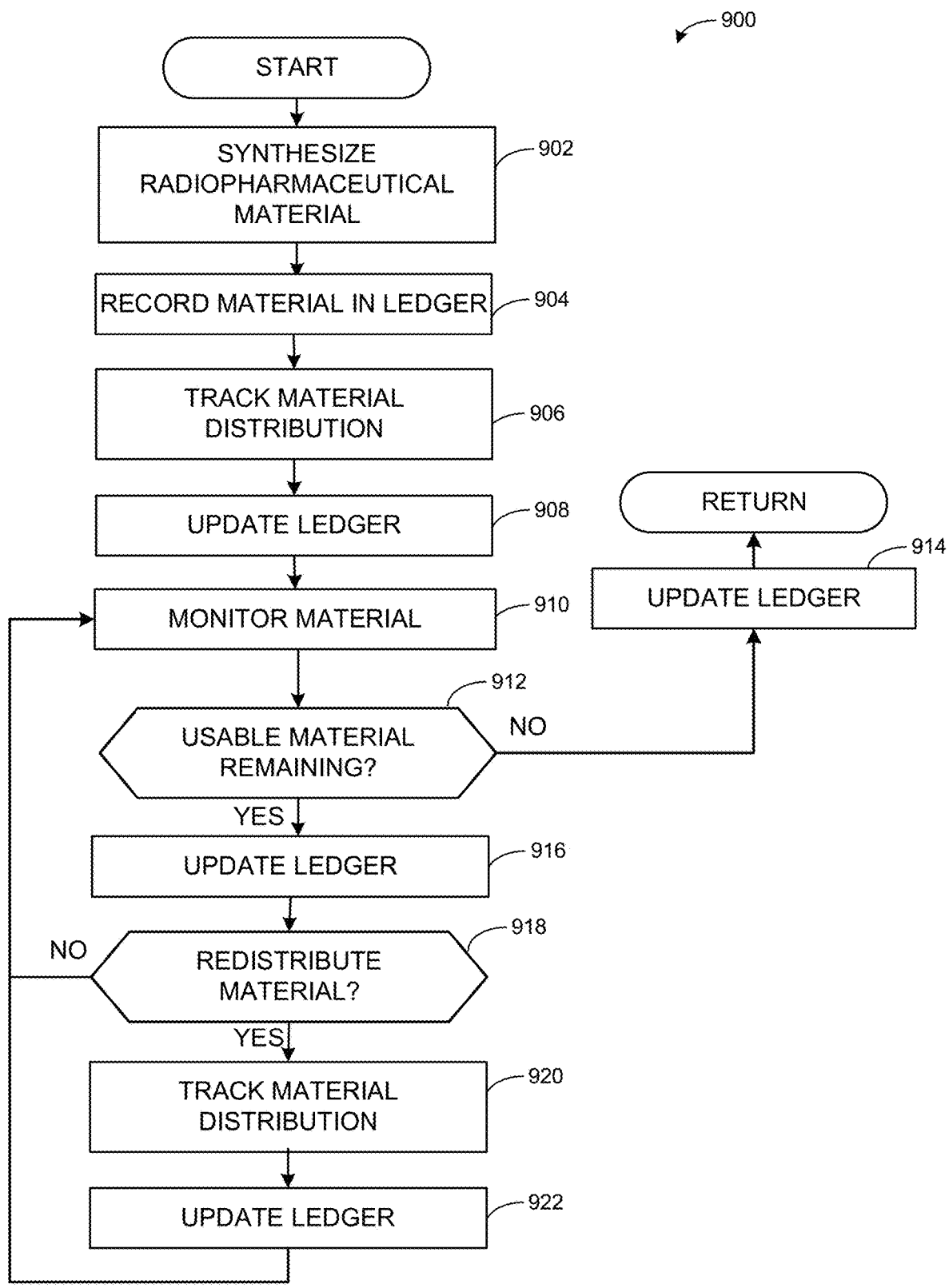
FIG. 9 illustrates a flow diagram of an example method to manage radiopharmaceutical generators and monitor radiopharmaceutical material synthesized by the generators.

A flowchart representative of example machine readable instructions for implementing components disclosed and described herein are shown in conjunction with at least FIGS. 1-8 is shown in the example of FIG. 9. In the examples, the machine readable instructions include a program for execution by a processor such as the processor 1012 shown in the example processor platform 800 discussed below in connection with FIG. 10. The program may be embodied in machine readable instructions stored on a tangible computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowcharts illustrated in conjunction with at least FIGS. 1-8, many other methods of implementing the components disclosed and described herein may alternatively be used. For example, the order of execution of the blocks may be changed, and/or some of the blocks described may be changed, eliminated, or combined. Although the flowcharts of at least FIGS. 1-8 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) of at least FIG. 9 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of at least FIG. 9 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

FIG. 9 illustrates a flow diagram of an example method 900 to manage radiopharmaceutical generators and monitor radiopharmaceutical material synthesized by the generators. At block 902, radiopharmaceutical material is synthesized. For example, the generator 210, such as a FASTlab™ or Drytec™ generator apparatus, synthesizes a batch of radioisotopes to be used in PET imaging at a hospital. At block 904, the material is recorded in the distributed ledger 300. For example, a record 310-330 can be created in the ledger 300 including a type of material, an amount of material, a time of material creation and/or release, an intended recipient/purchaser/customer of the material, etc. At block 906, distribution of the material to the intended recipient is tracked via the ledger 300 (e.g., by updating and/or creating a new record 310-330 with the location, quantity, usable life, etc., of the material, by adding a transaction 316-337 to the record 310-330, etc.). For example, an imaging center is sent the radioimaging material for nuclear imaging at the center.

At block 908, the ledger 300 is updated based on the distributed material. For example, the record 310-330 associated with the batch of material can be adjusted as the material ages and its usability decreases per its half-life. The record 310-330 can be updated with a transaction 316-337 and/or a new record 310-330 created based on a remainder of the material left after use by the customer, for example. The record 310-330 can be updated based on a location of the material, for example. At block 910, the material is monitored. Thus, decrease in usable life, change in location, change in amount, change in status (e.g., in use, for sale, etc.), etc., are monitored and noted (e.g., by the distribution monitoring processor 220, the remote server 230, the customer subsystem 240-245, etc.).

At block 912, the monitored material is evaluated to determine whether usable material remains. If not enough usable material remains (e.g., insufficient usable material for a nuclear imaging procedure, etc.), then, at block 914, the record 310-330 associated with the material in ledger 300 is updated (e.g., by adding a transaction 316-337 to the record, etc.), and the process 900 returns.

However, if usable material remains, then, at block 916, the ledger 300 is updated such that the record 310-330 (e.g., an existing record and/or a new record) reflects the status (e.g., quantity, elapsed time, time remaining, location, next destination, etc.) of the material. At block 918, the material and its associated record 310-330 are evaluated to determine whether a next destination is available for redistribution of the material. For example, customer A may have sold the remaining material to customer B, the supplier to customer A may have sold the remainder to customer B, customers A and B may have jointly purchased material and customer A is now to provide the remainder to B, etc. If the material is to be redistributed, then, at block 920, the distribution of the material is tracked via the ledger 300 (e.g., by updating and/or creating a new record 310-330 with the location, quantity, usable life, etc., of the material). At block 922, the ledger 300 is updated based on its usage at its new location (e.g., by adding a transaction 316-337 to the record 310-330, etc.).

Figure 10:
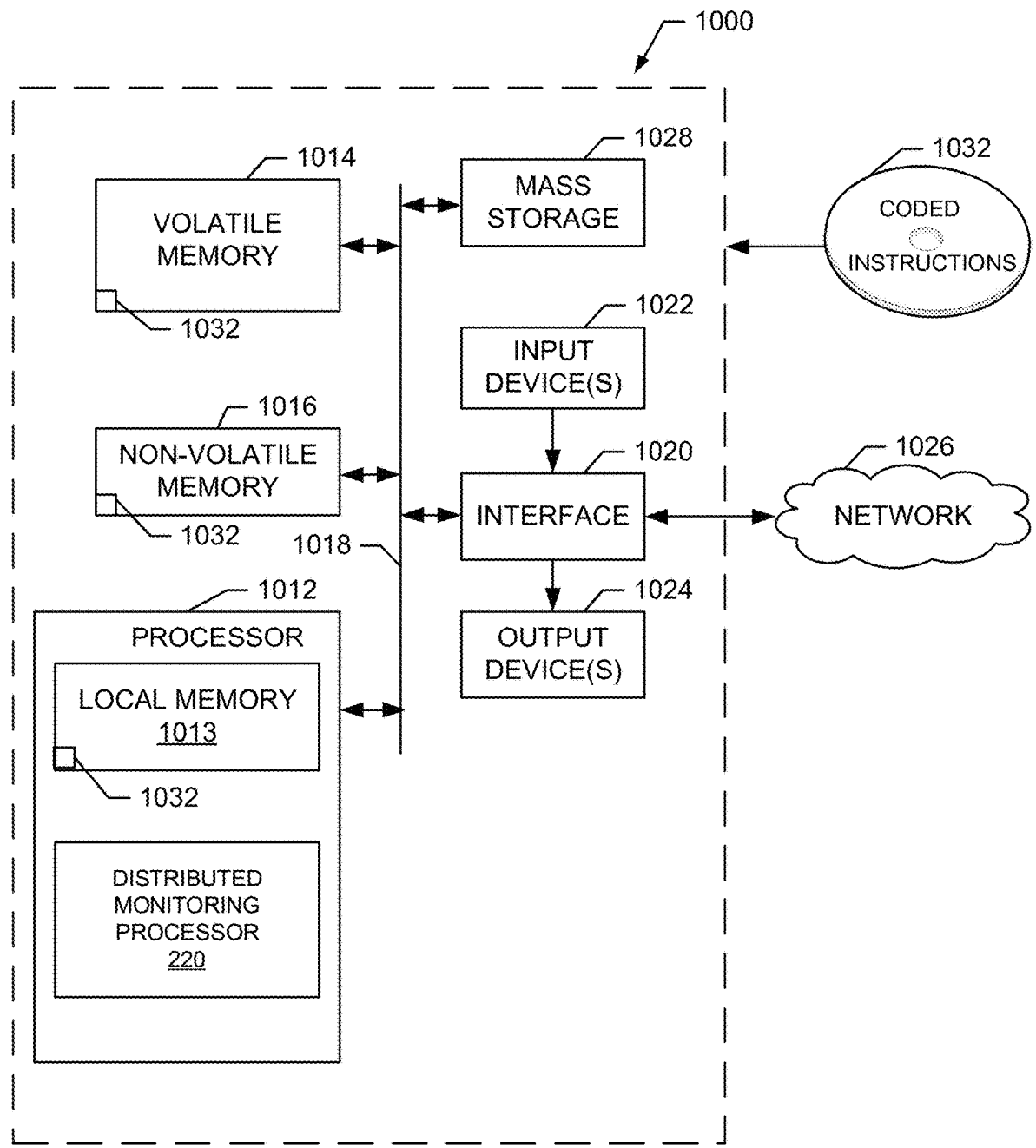
FIG. 10 is a block diagram of a processor platform structured to execute the example machine readable instructions to implement components disclosed and described herein.

FIG. 10 is a block diagram of an example processor platform 1000 structured to executing the instructions of at least FIG. 9 to implement the example components disclosed and described herein with respect to FIGS. 1-8. The processor platform 1000 can be, for example, a server, a personal computer, a mobile device (e.g., a cell phone, a smart phone, a tablet such as an iPad™), a personal digital assistant (PDA), an Internet appliance, or any other type of computing device.

The processor platform 1000 of the illustrated example includes a processor 1012. The processor 1012 of the illustrated example is hardware. For example, the processor 1012 can be implemented by integrated circuits, logic circuits, microprocessors or controllers from any desired family or manufacturer.

The processor 1012 of the illustrated example includes a local memory 1013 (e.g., a cache). The example processor 1012 of FIG. 10 executes the instructions of at least FIG. 9 to implement the systems and infrastructure and associated methods of FIGS. 1-8 such as the example controller 212, the example distribution monitoring processor 220, the example remote server 230, the example customer subsystems 240-245, the example distributed ledger 300, the example smart contract 500, or, more generally, the example system 200, etc. The processor 1012 of the illustrated example is in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 is controlled by a clock controller.

The processor platform 1000 of the illustrated example also includes an interface circuit 1020. The interface circuit 1020 may be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit(s) a user to enter data and commands into the processor 1012. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1020 of the illustrated example, thus, typically includes a graphics driver card, a graphics driver chip or a graphics driver processor.

The interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1032 of FIG. 10 may be stored in the mass storage device 1028, in the volatile memory 1014, in the non-volatile memory 1016, and/or on a removable tangible computer readable storage medium such as a CD or DVD.

Figure 11:
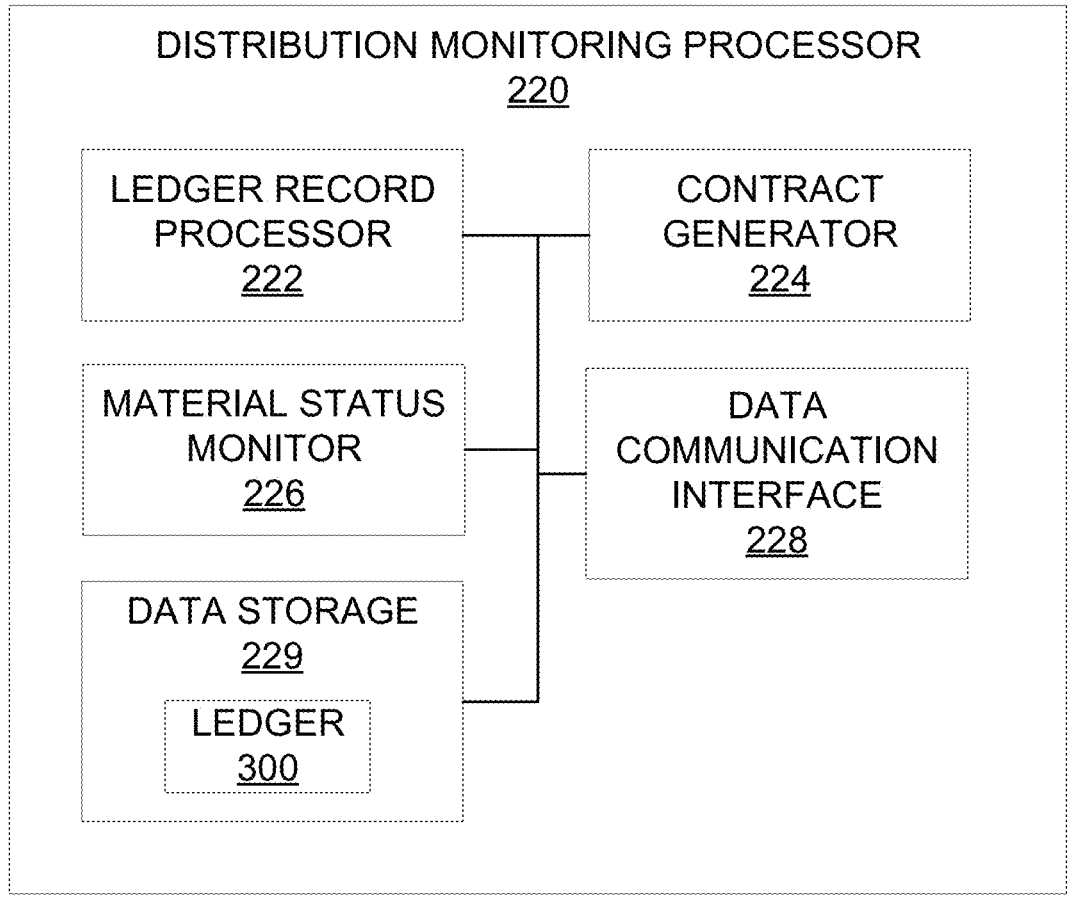
FIG. 11 illustrates an example schematic implementation of the distribution monitoring processor of the example of FIG. 2.

As shown in the example of FIG. 1, the distribution monitoring processor 220 can be implemented using a ledger record processor 222, a contract generator 224, a material status monitor 226, a data communication interface 228, and a data storage 229 to store data, instructions, etc., including a copy of the ledger 300. In the example of FIG. 11, the ledger record processor 222 is to create, modify, and/or otherwise process records 310-330 in the distributed ledger 300. Updates to the ledger 300 can be communicated to other devices 230, 240, 245 having copies of the distributed ledger 300 via the communication interface 228, for example. The example contract generator 224 can generate, modify, and/or otherwise process smart contracts 500 involving the generator 210, synthesized material, etc. The example material status monitor 226 can communicate via the data communication interface 228 to gather information from the generator 210, remote server 230, customer subsystem 240, 245, etc., to track status of the radiopharmaceutical material such as location, quantity, elapsed time, etc. The material status monitor 226 can provide updates to the ledger record processor 222, the contract generator 224, etc. The data communication interface 228 facilitates the exchange of information, instructions, verification, other feedback, etc., between the generator 210, the processor 220, the remote server 230, the customer subsystem 240-245, etc. The data storage 229 stores the processor's 220 copy of the distributed ledger 300 along with other data, operating instructions, configuration parameters, etc.

From the foregoing, it will be appreciated that the above disclosed methods, apparatus, and articles of manufacture have been disclosed to implement a distributed ledger tracking radiopharmaceutical material, generators, and/or other equipment and enabling distribution, usage, and/or rental agreements and supplemental/secondary agreements for use of material, generator, etc. The disclosed methods, apparatus and articles of manufacture improve the operation of a radiopharmaceutical generator and/or other computing device by enabling it to quantify, track, and manipulate synthesized radiopharmaceutical material and coordinate with a remote server and/or customer subsystems via a processor to manage decaying radiopharmaceutical material. The disclosed methods, apparatus and articles of manufacture are accordingly directed to one or more improvement(s) in the functioning of a computer and/or computing device including a radiopharmaceutical generator, monitoring processor, etc.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A distribution monitoring processor apparatus comprising:

a data storage to store instructions for execution and a first copy of a distributed ledger;

a data communication interface to receive and transmit data, in communication with a radiopharmaceutical material generator to synthesize a batch of radiopharmaceutical material;

a material status monitor to track a status of the batch of radiopharmaceutical material, the material status monitor to receive an indication of a type, a quantity, and a timestamp associated with the batch of radiopharmaceutical material from the radiopharmaceutical material generator via the data communication interface; and a ledger record processor triggered by the indication from the radiopharmaceutical material generator to generate and update a record in the first copy of the distributed ledger using the indication of type, quantity, and timestamp associated with the batch of radiopharmaceutical material from the material status monitor, the ledger record processor to add a transaction to the record to track when and what quantity of the batch of radiopharmaceutical material is sold to a first customer and resold to a second customer, wherein the material status monitor is to track a first use of the batch of radiopharmaceutical material by the first customer and to track, based on the indication from the radiopharmaceutical material generator, usable life of a remainder of the batch of radiopharmaceutical material after the first use to update the record with a first update in the first copy of the distributed ledger with the ledger record processor to reflect a remaining quantity and usable life of the remainder of the batch of radiopharmaceutical material after the first use via a transaction added to the record, the remainder of the batch of radiopharmaceutical material to be resold to the second customer in association with a second update to the record, and wherein the material status monitor is to inactivate the record from the distributed ledger in response to determining, based on the tracking of use and the usable life, that the remainder of the batch of radiopharmaceutical material is unusable.

2. The apparatus of claim 1, further including a contract generator to generate smart contract to involve the batch of radiopharmaceutical material and a customer subsystem associated with a first customer, the first customer to receive the batch of radiopharmaceutical material, the smart contract to facilitate requesting, selling, and reselling the batch of radiopharmaceutical material via the smart contract including reselling of a portion of the batch of radiopharmaceutical material to a second customer.

3. The apparatus of claim 2, wherein the smart contract is to include a function to trigger the radiopharmaceutical material generator to synthesize the batch of radiopharmaceutical material.

4. The apparatus of claim 1, wherein the ledger record processor is to communicate an update to the record of the first copy of the distributed ledger to at least one of a remote server or a customer subsystem via the data communication interface.

5. The apparatus of claim 4, wherein the at least one of the remote server or the customer subsystem is to verify the update to the record of the first copy of the distributed ledger.

6. The apparatus of claim 1, wherein the material status monitor is to be connected to the radiopharmaceutical material generator to trigger the ledger record processor to generate the record based on synthesis of the batch of radiopharmaceutical material by the radiopharmaceutical material generator.

7. The apparatus of claim 1, wherein the batch of radiopharmaceutical material includes radiopharmaceutical material for position emission tomography.

8. A non-transitory computer-readable storage medium including instructions which, when executed, cause at least one processor to at least:
track a status of a batch of radiopharmaceutical material synthesized by a radiopharmaceutical material generator in communication with the at least one processor, the status to include a type, a quantity, and a timestamp associated with the batch of radiopharmaceutical material;
generate, triggered by the status from the radiopharmaceutical material generator, a record in a first copy of a distributed ledger using the type, quantity, and timestamp associated with the batch of radiopharmaceutical material;
update the record based on at least one of usage of the batch of radiopharmaceutical material to a first customer, resale of at least a portion of the batch of radiopharmaceutical material to a second customer, and decay of the batch of radiopharmaceutical material;
share the record with a second copy of the distributed ledger;
track a first use of the batch of radiopharmaceutical material and track, based on the status from the radiopharmaceutical material generator, usable life of a remainder of the batch of radiopharmaceutical material after the first use to update the record in the first copy of the distributed ledger to reflect a remaining quantity and usable life of the remainder of the batch of radiopharmaceutical material after the first use via a transaction added to the record; and
inactivate the record in response to determining, based on the tracking, that the remainder of the batch of radiopharmaceutical material is unusable.

9. The computer-readable storage medium of claim 8, wherein the instructions, when executed, further cause the at least one processor to at least generate a smart contract to involve the batch of radiopharmaceutical material and a customer subsystem associated with a first customer, the first customer to receive the batch of radiopharmaceutical material, the smart contract to facilitate requesting, selling, and reselling the batch of radiopharmaceutical material via the smart contract including reselling of a portion of the batch of radiopharmaceutical material to a second customer.

10. The computer-readable storage medium of claim 9, wherein the smart contract is to include a function to trigger the radiopharmaceutical material generator to synthesize the batch of radiopharmaceutical material.

11. The computer-readable storage medium of claim 8, wherein the instructions, when executed, cause the at least one processor to at least communicate an update to the record of the first copy of the distributed ledger to at least one of a remote server or a customer subsystem.

12. The computer-readable storage medium of claim 11, wherein the instructions, when executed, cause the at least one processor to at least verify the update to the record based on feedback from at least one of the remote server or the customer subsystem.

13. The computer-readable storage medium of claim 8, wherein the instructions, when executed, cause the at least one processor to generate the record during synthesis of the batch of radiopharmaceutical material by a generator in communication with the at least one processor.

14. A computer-implemented method of managing radiopharmaceutical material, the method comprising:
tracking, using at least one processor, a status of a batch of radiopharmaceutical material synthesized by a radiopharmaceutical material generator in communication with the at least one processor, the status to include a type, a quantity, and a timestamp associated with the batch of radiopharmaceutical material;
generating, using the at least one processor triggered by the status from the radiopharmaceutical material generator, a record in a first copy of a distributed ledger using the type, quantity, and timestamp associated with the batch of radiopharmaceutical material;
updating, using the at least one processor, the record based on at least one of usage of the batch of radiopharmaceutical material by a first customer, resale of at least a portion of the batch of radiopharmaceutical material to a second customer, and decay of the batch of radiopharmaceutical material; and
sharing, using the at least one processor, the record with a second copy of the distributed ledger;
tracking, using the at least one processor, a first use of the batch of radiopharmaceutical material and tracking, based on the status from the radiopharmaceutical material generator, usable life of a remainder of the batch of radiopharmaceutical material after the first use to update the record in the first copy of the distributed ledger to reflect a remaining quantity and usable life of the remainder of the batch of radiopharmaceutical material after the first use via a transaction added to the record; and
inactivating the record in response to determining, based on the tracking, that the remainder of the batch of radiopharmaceutical material is unusable.

15. The method of claim 14, further including generating a smart contract to involve the batch of radiopharmaceutical material and a customer subsystem associated with a first customer, the first customer to receive the batch of radiopharmaceutical material, the smart contract to facilitate requesting, selling, and reselling the batch of radiopharmaceutical material via the smart contract including reselling of a portion of the batch of radiopharmaceutical material to a second customer.

16. The method of claim 15, further including triggering, via a function of the smart contract, the radiopharmaceutical material generator to synthesize the batch of radiopharmaceutical material.

17. The method of claim 14, further including communicating an update to the record of the first copy of the distributed ledger to at least one of a remote server or a customer subsystem.

\* \* \* \* \*